United States Patent [19]

Cracknell

[11] Patent Number: 5,643,902
[45] Date of Patent: Jul. 1, 1997

[54] VETERINARY TREATMENT

[75] Inventor: Victor Charles Cracknell, Tadworth, England

[73] Assignee: Pfizer Inc., New York, N.Y.

[21] Appl. No.: 214,653

[22] Filed: Mar. 16, 1994

Related U.S. Application Data

[63] Continuation of Ser. No. 934,754, filed as PCT/GB91/00635, Apr. 22, 1991, abandoned.

[30] Foreign Application Priority Data

Apr. 26, 1990 [GB] United Kingdom ............ 9009446

[51] Int. Cl.$^6$ ............ A61K 31/43; A61K 31/545; A61K 31/395
[52] U.S. Cl. ............ 514/192; 514/198; 514/199; 514/200; 514/210
[58] Field of Search .................. 514/192, 198, 514/199, 200, 210

[56] References Cited

U.S. PATENT DOCUMENTS

| | | | |
|---|---|---|---|
| 4,098,897 | 7/1978 | Howarth | 514/210 |
| 4,537,887 | 8/1985 | Rooke et al. | 514/210 |
| 4,562,182 | 12/1985 | Harbridge et al. | 514/210 |

FOREIGN PATENT DOCUMENTS

| | | |
|---|---|---|
| 0010904 | 5/1980 | European Pat. Off. . |
| 2005538 | 5/1982 | United Kingdom . |

OTHER PUBLICATIONS

Brogden et al., "Amoxycillin/Clavulanic Acid: A Review of its Antibacterial Activity, Pharmacokinetics and Therapeutic Use", Drugs 22: 337–362 (1981).

Unlisted Drugs, vol. 37, No. 1, Jan. 1985, (Chatham, New Jersey, US)—see p. 13, abstract e, "Synulox".

Unlisted Drugs, vol. 38, No. 6, Jun. 1986, (Chatham, New Jersey, US)—see abstract, "Clavamox".

Poster Presentation, IPVS, Lausanne, Jul. 1990. Webster el al.

The Veterinary Record, Apr. 14, 1990, p. 363.

Primary Examiner—Kevin E. Weddington
Attorney, Agent, or Firm—Peter C. Richardson; Paul H. Ginsburg; Alan L. Koller

[57] ABSTRACT

A formulation comprising amoxycillin or a veterinarily acceptable derivative thereof, clavulanic acid or a veterinarily acceptable derivative thereof, and a veterinarily acceptable carrier is used in the treatment of farrowing fever and/or bacterial pneumonia in pigs.

5 Claims, 2 Drawing Sheets

VETERINARY TREATMENT

This is a continuation of application Ser. No. 07/934,754, filed as PCT/GB91/00635 Apr. 22, 1991; now abandoned.

This invention relates to a method for the treatment of bacterial infections in pigs, particularly those infections associated with farrowing fever and bacterial pneumonia.

GB-B-2 005 538 describes a dry pharmaceutical composition, which comprises 20 mg to 1500 mg of amoxycillin trihydrate, 20 mg to 500 mg of potassium clavulanate and a pharmaceutically acceptable carrier, with the proviso that the weight ratio of amoxycillin trihydrate to potassium clavulanate is from 6:1 to 1:1.

According to the present invention there is provided a method for the treatment of farrowing fever and bacterial pneumonia in pigs, which comprises administering to the animal an effective amount of amoxycillin or a veterinarily acceptable derivative thereof, clavulanic acid or a veterinarily acceptable derivative thereof, and a veterinarily acceptable carrier.

A second aspect of the invention provides the use of a formulation comprising an effective amount of amoxycillin or a veterinarily acceptable derivative thereof, clavulanic acid or a veterinarily acceptable derivative thereof, and a veterinarily acceptable carrier in the manufacture of a medicament for use in the treatment of farrowing fever and bacterial pneumonia in pigs.

The formulation has notable bactericidal activity against the bacteria associated with the diseases farrowing fever and bacterial pneumonia in particular.

*Actinobacillus pleuropneumoniae.*

Suitably the clavulanic acid used in the formulation is in the form of a veterinarily acceptable salt such as potassium clavulanate.

Suitably the amoxycillin used in the formulation is in the form of the trihydrate or a veterinarily acceptable ester or salt of amoxycillin such as the sodium salt.

The preferred weight ratio of amoxycillin or derivative to clavulanic acid or derivative is from 6:1 to 1:1.

Advantageously, a liquid formulation of the invention comprises 36 mg/ml clavulanic acid (as potassium clavulanate) and 140 mg/ml amoxycillin (as amoxycillin trihydrate).

Preferred veterinarily acceptable carriers include for example veterinarily acceptable oils such as mineral oils or fractionated coconut oil such as Miglyol 840.

Suitably the formulation is administered to the animal by intramuscular injection.

The formulation is typically prepared as an off-white suspension and is presented as a 'Ready-To-Use' form, that is the formulation is preprepared and packed in a suitable container, wherein it is ready for administration to the animal in need thereof.

The dosage rate will vary according to the size of the animal. A suitable dosage rate is generally between 2 and 25 mg/kg bodyweight of the animal, for example about 8.75 mg/kg.

Typically more than a single dose of the formulation will be required for the treatment of the bacterial infections, suitably one dose per day for 3 to 5 days is required. In cases of severe infections prolonged treatment may be required.

Veterinary formulations for use in the present invention may be prepared by mixing the ingredients thereof in the required proportions.

The formulation is then packaged into an appropriate container ready for administration.

The following Example illustrates the invention.

| Formulation | g/100 ml |
| --- | --- |
| amoxycillin trihydrate | 14.0 |
| potassium clavulanate | 3.6 |
| phenol | 0.5 |
| Miglyol 840 | to 100 ml |

Clinical data

CASE STUDY 1

Naturally-occuring cases of farrowing fever in pigs were diagnosed on clinical grounds, then treated on an alternating basis with either Synulox* or a control drug. The control drug was a penicillin G/streptomycin mixture. Treatment was administered once daily for a minimum of 3 days. Synulox* was given at a dose rate of 1 ml per 20 kg of body weight.

The clinical response to treatment was scored on a predefined scale:

CRS 1=excellent

CRS 2=food

CRS 3=fair

CRS 4=poor (CRS=clinical response score)

Figure 1:
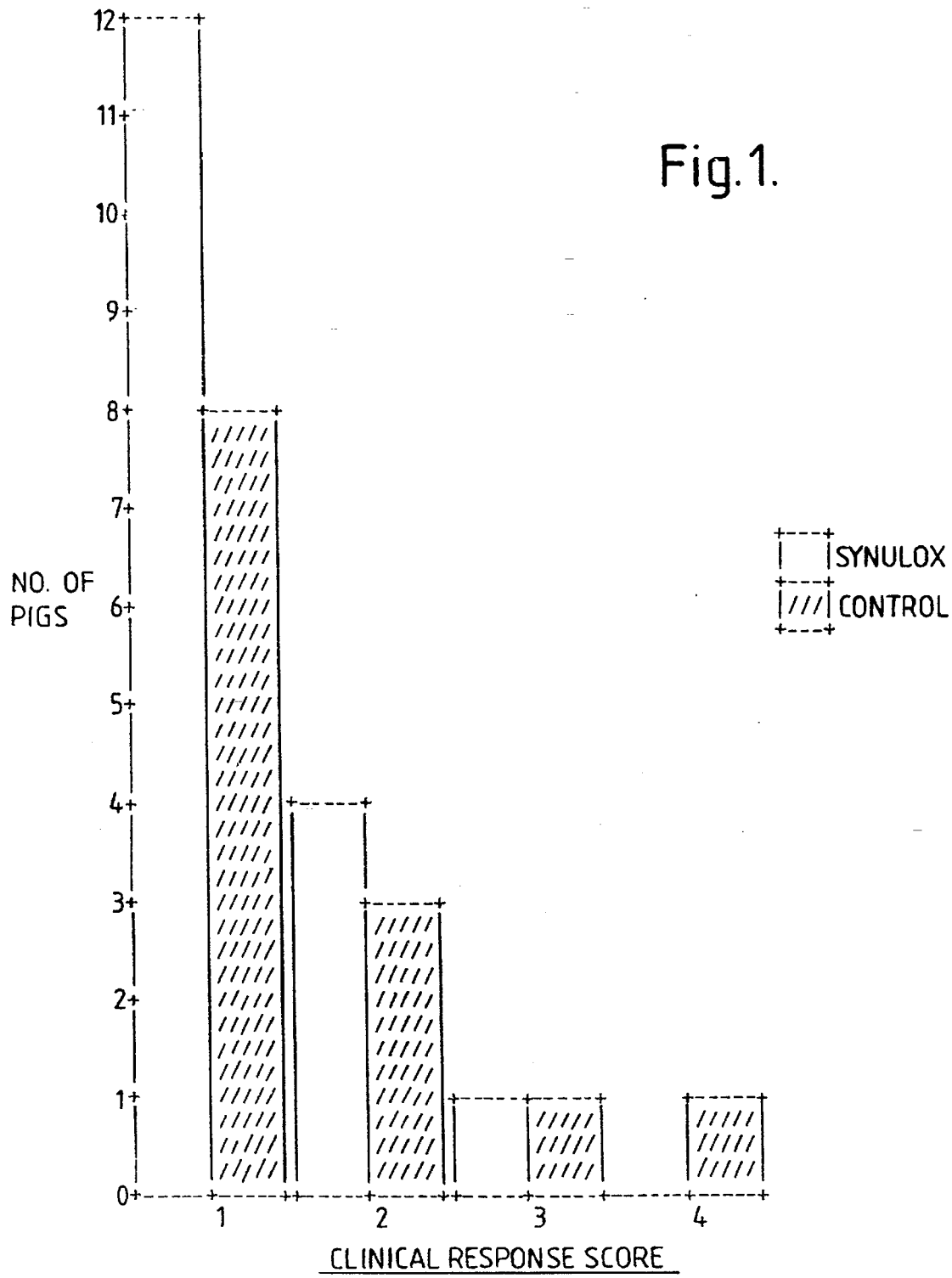
FIG. 1 shows clinical responses of pigs with farrowing fever to treatment with synulox or control.

From the results which are summarised in FIG. 1, it can be seen that Synulox* has good efficacy in the treatment of farrowing fever in pigs.

CASE STUDY 2

A total of 229 pigs with pneumonia caused by *Actinobacillus (Haemophilus) pleuropneumonia* were involved in this study.

156 pigs were treated with Synulox* and 73 were treated with a control drug, oxytetracycline (1 ml/kg body weight administered intramuscularly). Synulox* was injected intramuscularly at a dose rate of 1 ml/20 kg body weight. Treatment was continued daily until clinical signs of cough, dyspnoea, anorexia and depression were remitted and clinical responses were stored on the basis of the number of treatments required to achieve remissision. Clinical response was scored as follows:

CRS 1=excellent

CRS 2=good

CRS 3=fair

CRS 4=poor

Figure 2:
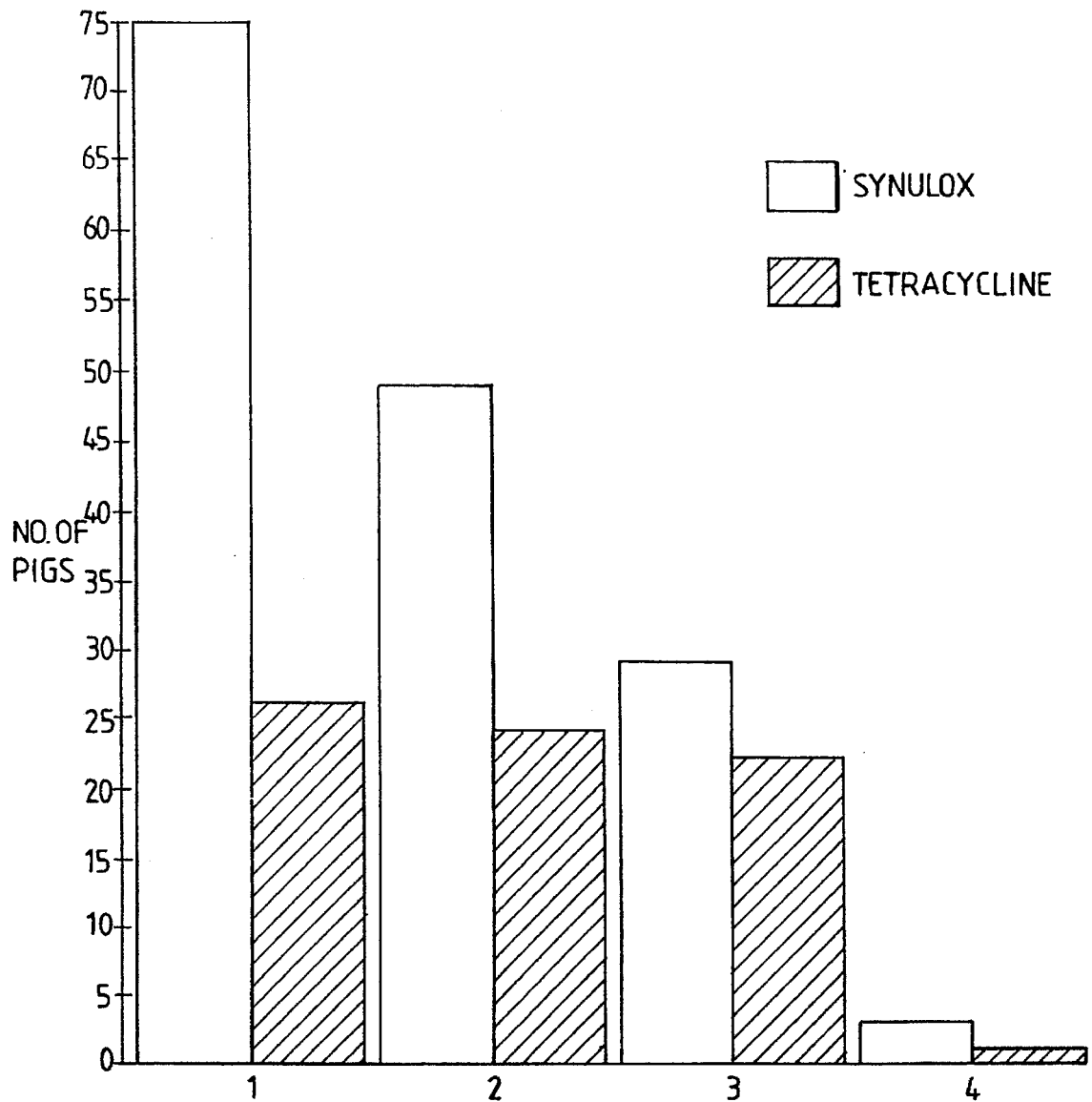
FIG. 2 shows clinical responses of pneumonic pigs to treatment with synulox or tetracycline.

The clinical response scores are summarised in FIG. 2, wherein it was shown that of the total of 156 pigs treated with Synulox* 48.1% showed an "excellent" response, 31.4% had a "good" response, 18.6% "fair" and only 1.9% "poor" against 35.6% of pigs treated with the control showing an "excellent" response 32.9%, "good", 31.5% "fair" and 0% "poor". It was therefore concluded that Synulox* has good efficacy in the treatment of bacterial pneumonia in pigs.

\* Synulox is a Trademark of Beecham Group p.l.c. Synulox Synulox is an oily suspension containing 35 mg/ml clavulanic acid (K salt) and 140 mg/ml amoxycillin (trihydrate).

I claim:

1. A method for the treatment of farrowing fever and/or bacterial pneumonia in pigs, which comprises administering to the animal an effective amount of amoxycillin or a veterinary acceptable derivative thereof, clavulanic acid or a veterinary acceptable derivative thereof, and a veterinary acceptable carrier.

2. A method according to claim 1 wherein the clavulanic acid is used in the form of potassium clavulanate.

3. A method according to claim 1 or 2 wherein amoxycillin is used in the form of trihydrate or the sodium salt.

4. A method according to claim 1, 2 or 3 wherein the weight ratio of amoxycillin or derivative to clavulanic acid or derivative is from 6:1 to 1:1.

5. A method according to claim 1 wherein the veterinarily acceptable carrier is an oil suitable for injection.

* * * * *